United States Patent [19]
Trantow et al.

[11] Patent Number: 6,075,593
[45] Date of Patent: Jun. 13, 2000

[54] METHOD FOR MONITORING AND CONTROLLING LASER SHOCK PEENING USING TEMPORAL LIGHT SPECTRUM ANALYSIS

[75] Inventors: Richard L. Trantow; Ui W. Suh, both of Cincinnati, Ohio

[73] Assignee: General Electric Company, Cincinnati, Ohio

[21] Appl. No.: 09/365,887

[22] Filed: Aug. 3, 1999

[51] Int. Cl.[7] .......................... G01N 21/63; G01N 21/88
[52] U.S. Cl. ........................................ 356/318; 356/237.1
[58] Field of Search .................................. 356/316, 317, 356/318, 237.1, 237.2

[56] References Cited

U.S. PATENT DOCUMENTS

| | | |
|---|---|---|
| 4,060,327 | 11/1977 | Jacobowitz et al. . |
| 4,299,488 | 11/1981 | Tomlinson, III . |
| 4,542,290 | 9/1985 | Tan et al. . |
| 4,630,925 | 12/1986 | Schiller et al. . |
| 4,958,231 | 9/1990 | Tsuchiya . |
| 5,051,790 | 9/1991 | Mannava et al. ........................ 148/510 |
| 5,225,894 | 7/1993 | Nicholson et al. . |
| 5,347,460 | 9/1994 | Gifford et al. . |
| 5,703,357 | 12/1997 | Shih et al. . |
| 5,849,162 | 12/1998 | Bartolomei et al. . |
| 5,948,293 | 9/1999 | Somers et al. ...................... 219/121.85 |

OTHER PUBLICATIONS

"Laser Shocking extends fatigue life", by John A. Vaccari, American Machinist, Jul. 1992, pp. 62–64.

"Laser Shock Processing Increases the Fatigue Life of Metal parts", Materials and Processing Report, Sep. 1991, pp. 3–5.

"New Results In Measuring The Shot Peen Interface In Ti6A14V By Eddy Current", by Schoening, Jr., Soules, Thesling, and Politzer, Presented at the Shot Peening National Conference, Jul. 16–17, 1991, Los Angeles, California, 11 pages.

"X–Ray Diffraction Characterization of Residual Stresses Produced by Shot Peening", by Paul S. Prevey, President, Director of Research, Inc., pp. 81–93. (undated).

"Full Assurance Shot Peening Of Aircraft Gas Turbine Engine components", by Bailey, Lombardo, Popp, and Thompson, pp. 320–327. (undated).

"Residual Stress Measurement For Quality Control Of Shot Peening", Lambda Research, 2 pages. (undated).

*Primary Examiner*—F. L. Evans
*Attorney, Agent, or Firm*—Andrew C. Hess; Gerry S. Gressel

[57] ABSTRACT

A method for quality assurance of a laser shock peening process of workpieces includes measuring and recording or temporal light intensity data over a short period during the duration of a plasma associated with the vaporized material from laser shots fired during a production laser shock peening process. The recorded temporal data is then analyzed to obtain an instantaneous optical spectrum of the plasma and then used to provide statistical control of the production laser shock peening process. One correlation function of the present invention is based on a time integrated spectral peak intensity wavelength curve for each of the laser firings and for which a peak intensity wavelength is determined for a plurality of times during each plasma of a plurality or all of the firings. Production results from the analysis of the instantaneous optical spectrum is used to determine whether the production laser shock peening process is acceptable. One embodiment of the method compares the production results from the analysis of the instantaneous optical spectrum to a correlation of test results from the analysis of instantaneous optical spectrum and high cycle fatigue failure based on high cycle fatigue tests of test workpieces that are the same or related to the production workpieces and that were laser shock peened in the same or similar laser shock peening apparatus.

24 Claims, 9 Drawing Sheets

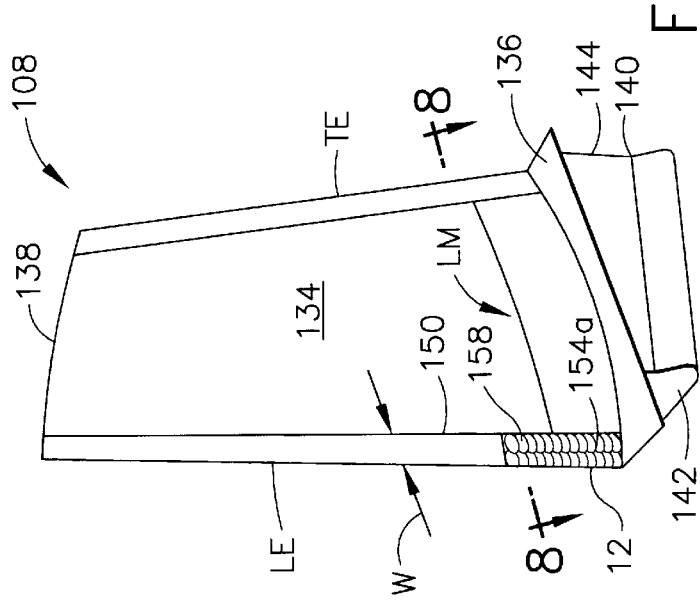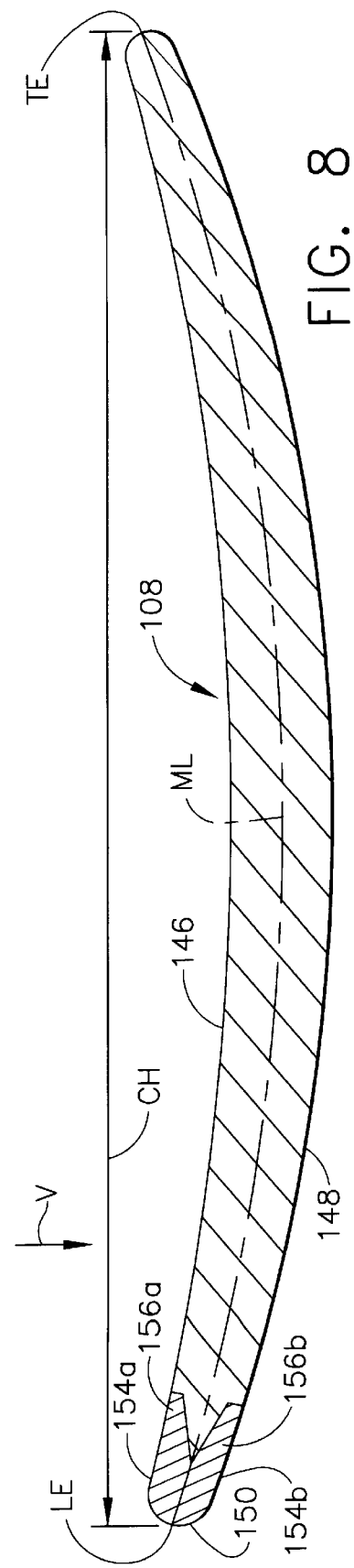

METHOD FOR MONITORING AND CONTROLLING LASER SHOCK PEENING USING TEMPORAL LIGHT SPECTRUM ANALYSIS

BACKGROUND OF THE INVENTION

1. Field of the Invention

This invention relates to process monitoring methods used for quality assurance of laser surface treatment of a metallic surface and, more particularly, a method for providing quality assurance of a laser shock peening (LSP) process by measuring a spectral intensity of light emitted by a laser generated plasma over its duration.

2. Description of Related Art

Laser shock peening or laser shock processing, as it is also referred to, is a process for producing a region of deep compressive residual stresses imparted by laser shock peening a surface area of a workpiece. Laser shock peening typically uses one or more radiation pulses from high power pulsed lasers to produce an intense shock wave at the surface of a workpiece similar to methods disclosed in U.S. Pat. No. 3,850,698 entitled "Altering Material Properties"; U.S. Pat. No. 4,401,477 entitled "Laser Shock Processing"; and U.S. Pat. No. 5,131,957 entitled "Material Properties". Laser shock peening, as understood in the art and as used herein, means utilizing a pulsed laser beam from a laser beam source to produce a strong localized compressive force on a portion of a surface by producing an explosive force at the impingement point of the laser beam by the instantaneous ablation or vaporization of a thin layer of that surface or of a coating (such as tape or paint) on that surface.

Laser peening has been utilized to create a compressively stressed protective layer at the outer surface of a workpiece which is known to considerably increase the resistance of the workpiece to fatigue failure as disclosed in U.S. Pat. No. 4,937,421 entitled "Laser Peening System and Method". These methods typically employ a curtain of water flowed over the workpiece or some other method to provide a confining plasma medium. This medium enables the plasma to rapidly achieve shockwave pressures that produce the plastic deformation and associated residual stress patterns that constitute the LSP effect.

Laser shock peening is being developed for many applications in the gas turbine engine field, some of which are disclosed in the following U.S. Pat. Nos.: 5,756,965 entitled "On The Fly Laser Shock Peening"; 5,591,009 entitled "Laser shock peened gas turbine engine fan blade edges"; 5,569,018 entitled "Technique to prevent or divert cracks"; 5,531,570 entitled "Distortion control for laser shock peened gas turbine engine compressor blade edges"; 5,492,447 entitled "Laser shock peened rotor components for turbomachinery"; 5,674,329 entitled "Adhesive tape covered laser shock peening"; and 5,674,328 entitled "Dry tape covered laser shock peening", all of which are assigned to the present Assignee. These applications, as well as others, are in need of an efficient quality assurance evaluation method for production runs using laser shock peening.

Laser shock peening processes have been developed to simultaneously LSP pressure and suction sides of leading and trailing edges of fan and compressor airfoils and blades as disclosed in U.S. Pat. No. 5,591,009 entitled "Laser shock peened gas turbine engine fan blade edges" and U.S. Pat. No. 5,531,570 entitled "Distortion control for laser shock peened gas turbine engine compressor blade edges". Single-sided shot peened Almen strips are well known for use in the field of shot peening quality control, see U.S. Pat. No. 2,620,838. However, Almen strips are not designed to provide a measure of the effect of a single laser beam impact. The LSP process involves the use of high pulse energy, short pulse duration laser systems. The combination of high energy and short duration, as well as variations in the stability of the beam path (such as at a water/air interface), limit the usefulness of electronic measurement systems to verify the true (calibrated) energy being delivered to the component being processed.

One laser shock peening quality assurance technique that has been used is high cycle fatigue (HCF) testing of blades having leading edges which have been LSP'd and notched in the LSP'd area before testing. This method is destructive of the testpiece, fairly expensive and time consuming to carry out, and significantly slows production and the process of qualifying LSP'd components. HCF testing is a random sampling technique and is a poor statistical quality measurement. An improved quality assurance method of measurement and control of the LSP process that is a non-destructive evaluation (NDE), inexpensive, accurate, and quick is highly desirable. It is also desirable to have an NDE quality assurance method that is relatively inexpensive and sufficiently economical to be used directly on the actual workpiece instead of indirectly on a sacrificial sampling of workpieces. LSP is a process that, as any production technique, involves machinery and is time consuming and expensive. Therefore, any techniques that can reduce the amount or complexity of production machinery and/or production time are highly desirable.

The present invention measures instantaneous spectral intensity of light emitted by a laser generated plasma over the temporal duration of a single firing of a laser used in the laser shock peening process. The invention preferably measures instantaneous light intensity of the plasma through the analysis of an instantaneous optical spectrum associated with vaporized material using optical devices such as a streak camera available from Hamamatsu of Japan.

SUMMARY OF THE INVENTION

A method of quality control for a production laser shock peening process of workpieces includes measuring and recording the instantaneous spectral light intensity over a short period during a duration of a plasma associated with vaporized material from individual laser shock peening laser shots fired during a production laser shock peening process. The recorded spectral temporal data is then analyzed to determine an instantaneous black body plasma spectrum and from that spectrum the plasma temperature over time which is then used to provide statistical control of the production laser shock peening process.

Production results from the analysis of the instantaneous optical spectrum is used to determine whether the production laser shock peening process is acceptable. One embodiment of the method compares the production results from the analysis of the instantaneous optical spectrum to a correlation of test results from the analysis of instantaneous optical spectrum and high cycle fatigue failure based on high cycle fatigue tests of test workpieces that are the same or related to the production workpieces and that were laser shock peened in the same or similar laser shock peening apparatus. In a more specific embodiment, each of the test workpieces has a failure precipitating flaw within a laser shock peened area of the test piece that was laser shock peened in the same or similar laser shock peening apparatus.

In one exemplary embodiment, the production workpieces are gas turbine engine blades having airfoils and the test workpiece is a gas turbine engine blade having an airfoil with a notch in a laser shock peened patch of the airfoil wherein the notch is formed after the airfoil has been laser shock peened. The analysis of instantaneous optical spectrum for the correlation is done for each laser pulse during the formation of the multi-pulse laser shock peened patch of the airfoil test workpieces.

The correlation in one embodiment of the present invention is a statistical fit of the optical spectrum radiated by a plasma, formed by the laser firing and measured during the formation and brief life of the plasma, to the shape of the classical black body spectrum. Another embodiment employs a comparison of an analysis of production results from the individual LSP events that make up the LSP'd area on the object to the statistical fit data relating the extension of the objects fatigue life to the dimension provided by the analysis of production results to determine whether the production laser shock peening process is acceptable.

ADVANTAGES

Advantages of the present invention are numerous and include lowering the cost, time, manpower and complexity of performing quality assurance tests during laser shock peening processes. Another advantage of the present invention is that it provides an in-process quality control that allows performing quality assurance tests during laser shock peening processes on the actual production parts and at the site of the process and in real time with respect to the processing. The present invention can help greatly reduce the amount of down-time for performing quality assurance tests during laser shock peening. The present invention replaces the tedious, costly and time consuming process of notched high cycle fatigue testing presently used for QA. The QA can be performed in tandem with an actual component or workpiece and is highly repeatable and, thus, very dependable as a QA process for laser shock peening.

The present invention has several other manufacturing advantages including measuring the laser energy at the component not raw energy of the laser prior to the beam passing through focusing and beam steering optics and through the air/water interface that alter the focus and energy distribution of the beam and lose energy. The present invention quickly and accurately measures the qualitative effect over a period of time of each plasma. The measuring devices of the present invention may be located near the processing location and be utilized frequently with real time results. The present invention provides a very dependable and accurate QA process due in a great part to its repeatability and lack of dependance on the amount of light captured by the optics of the detector.

BRIEF DESCRIPTION OF THE DRAWINGS

The foregoing aspects and other features of the invention are explained in the following description, taken in connection with the accompanying drawings where:

FIG. 7 is a perspective view of the fan blade in FIG. 1.

FIG. 8 is a cross-sectional view of the fan blade taken through line 8—8 in FIG. 7.

DETAILED DESCRIPTION OF THE INVENTION

Figure 1:
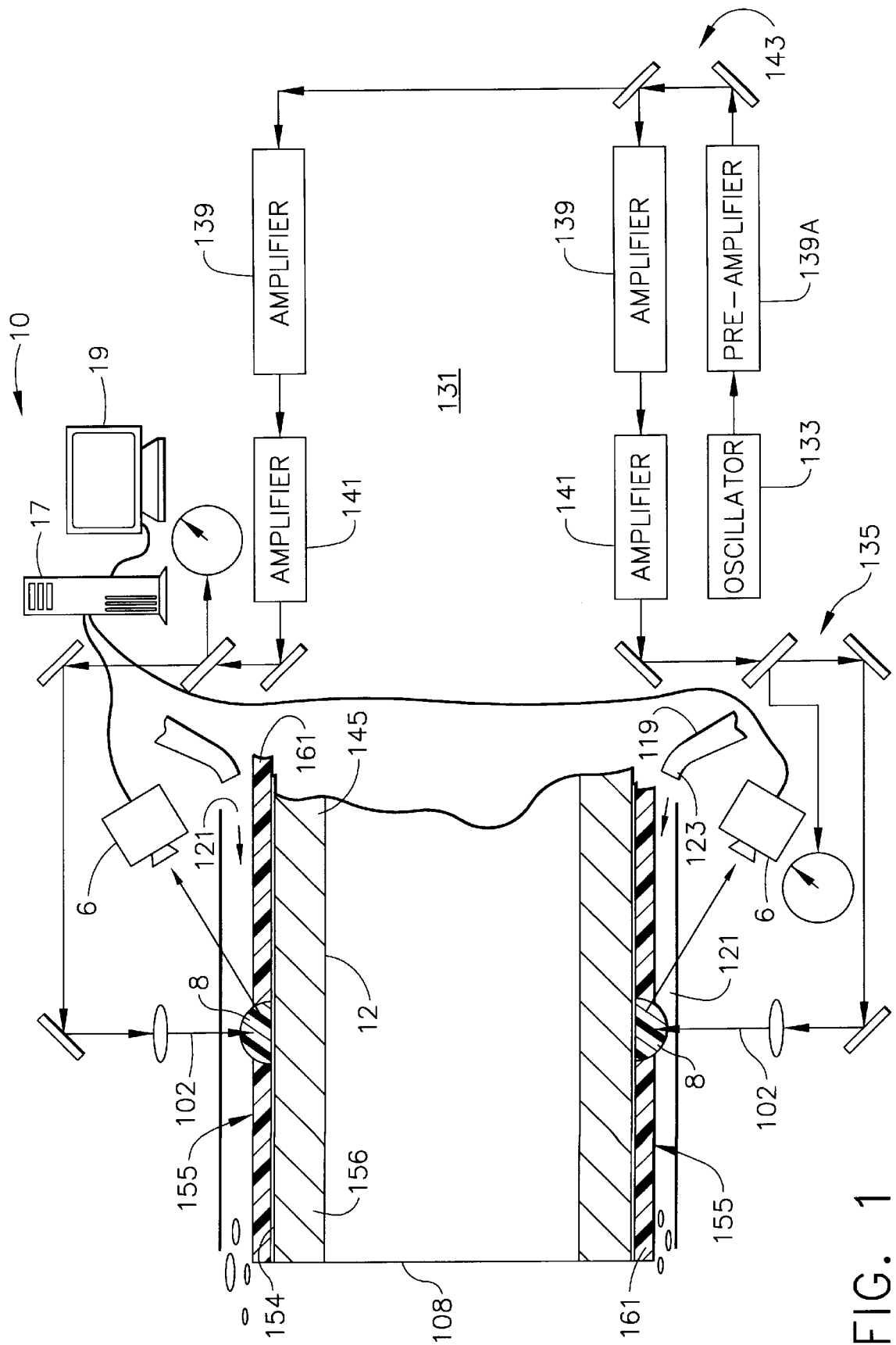
FIG. 1 is a schematic illustration of an exemplary embodiment of a system for measuring the spectral intensity over time of the light emitted by the plasma generated by a laser shock peening (LSP) process.

The present invention provides a quality assurance method for quality control of a laser shock peening process used for production workpieces exemplified in FIG. 1 by a production fan blade 108 (more fully illustrated in FIGS. 7 and 8) having a laser shock peened patch 12. Quality assurance is typically a go or no go, pass or fail, accept or reject type of test or analysis. The method and techniques of the present invention involves quality assurance of a laser shock peening process on a production workpiece such as an exemplary aircraft turbofan gas turbine engine fan blade or other object made of a metallic material as disclosed in U.S. Pat. Nos. 5,492,447, 5,674,329, 5,674,328, and 5,591,009. The method is a test which may be performed, preferably during or alternatively after, laser shock peening of each workpiece, or after or before a batch of workpieces are laser shock peened. Preferably, the present method tests every firing of the laser.

Illustrated in FIG. 1 is a laser beam 102 firing at a laser shock peened surface 154 within the laser shock peened area or patch 12 covered with an ablative coating 161 such as paint or an adhesive tape to form a coated surface 155 as disclosed in U.S. Pat. Nos. 5,674,329 and 5,674,328. The paint or tape provides an ablative medium, preferably over which is a clear containment medium, which may be a clear fluid curtain such as a flow of water 121. The ablative coating 161 is ablated generating a plasma 8 with each firing and, which in turn, results in a shock wave against on the surface of the metallic material of the blade or other object that may be used for testing the laser shock peening process. Other ablative materials may be used to coat the surface as suitable alternatives to paint. These coating materials include metallic foil or adhesive plastic tape as disclosed in U.S. Pat. Nos. 5,674,329 and 5,674,328.

These shock waves are re-directed towards the coated surface 155 by the curtain of flowing water 121 to generate shock waves (intense pressure waves) in the object being laser shock peened below the coated surface. The amplitude, shape, and quantity of these shockwaves determine the degree of plastic deformation incurred as a result of the LSP process, and the depth and intensity of the resultant compressive stresses. The ablative coating is used to protect the target surface and also to generate the plasma 8. In one exemplary application, the laser beam shock induced deep compressive residual stresses (in a compressive pre-stressed region 156) are generally about 50–150 KPSI (Kilo Pounds per Square Inch) extending from the laser shock peened surfaces 154 to a depth in a range of about 20–70 mils into the pre-stressed region 156.

Also illustrated in FIG. 1 is a schematic representation of an exemplary embodiment of a system 10 for measuring temporal light intensity of the plasma 8 generated during a single firing of a laser beam 102 during the laser shock peening process. The results derived from spectral/temporal light intensity data acquired using the system 10 are used to perform a quality assurance method for quality control of a laser shock peening process. A streak camera 6 or other means, such as a very fast line scan spectrometer, is used for making spectral/temporal measurements of optical spectrums (illustrated in FIG. 2) radiated by the plasma 8 at various points in a period of time PT during the duration of the plasma 8 from the firing of the laser beam 102.

Figure 2:
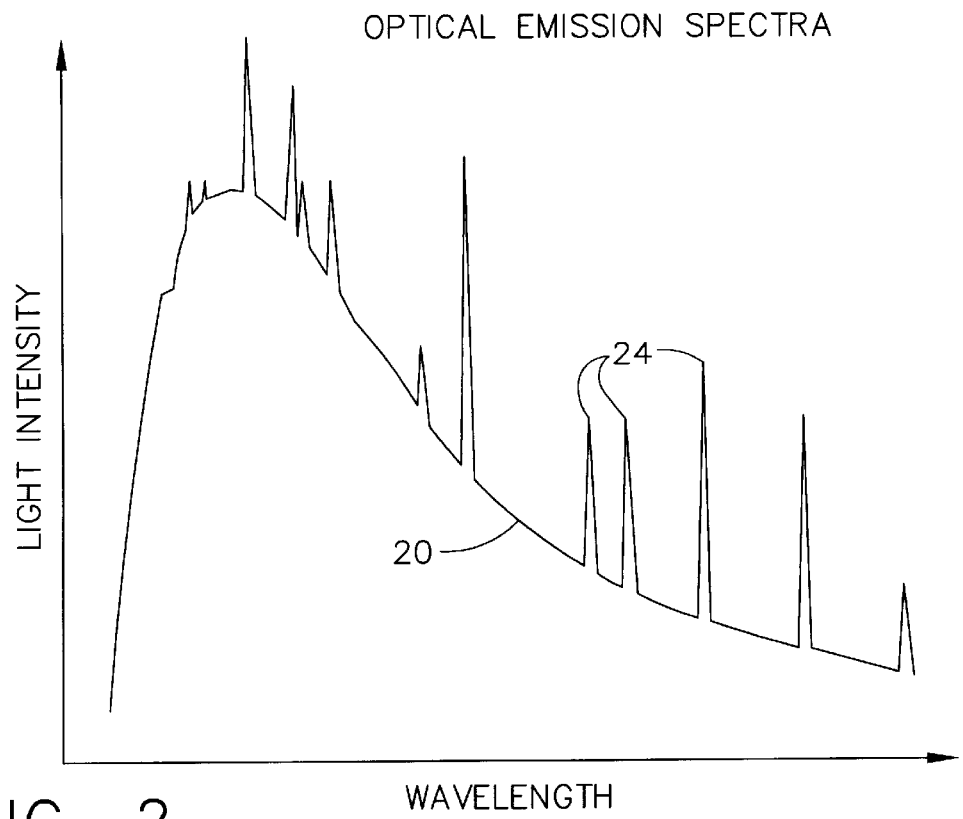
FIG. 2 is an exemplary graphical illustration of an optical emissions spectra from the plasma at a given point in time as measured by the system in FIG. 1.

The streak camera 6 records spectral light intensity data over time which is fed into a computer 17 for analysis of the data having a monitor 19 for display of the results. The computer is used to analyze the shape of the energy spectrum which represents the relative distribution of energy within this spectrum over very short time periods (potentially as short as 1 nano-second for laser pulse rise times of 5 nano-seconds) during the duration of the plasma. The generalized shape of the energy spectrum is illustrated in FIG. 2 where the optical emission spectra is shown as a light intensity graphed as a function of wavelength. The image of the optical spectrum emitted by the plasma is expected to contain both line structure and a generalized background distributed across the spectrum. The relative proportion of the energy that appears to be distributed between these two modes is dependent, in part, on the spectral resolution of the detector. The poorer the resolution, the more the line structure will be integrated into the general background. For black body radiators the spectral energy distribution of an incandescent source takes the form illustrated in FIG. 3. Whether the line structure is fully integrated or not, the energy distribution will contain a peak in the higher energy (shorter wavelength) end of the spectrum as in the case of black body radiation. That peak will be skewed torward the shorter wavelength end of the spectrum as temperature increases. In practice in one embodiment of the invention, a fit of the partially integrated spectral data to the idealized black body spectrum is used to determine an effective black body temperature throughout the duration of the plasma, which is related to the instantaneous pressure. During production runs measured optical spectrum data is compared to pre-determined optical spectrum criteria, preferably, in the form of a high cycle fatigue correlation for passing or failing the workpieces.

Figure 9:
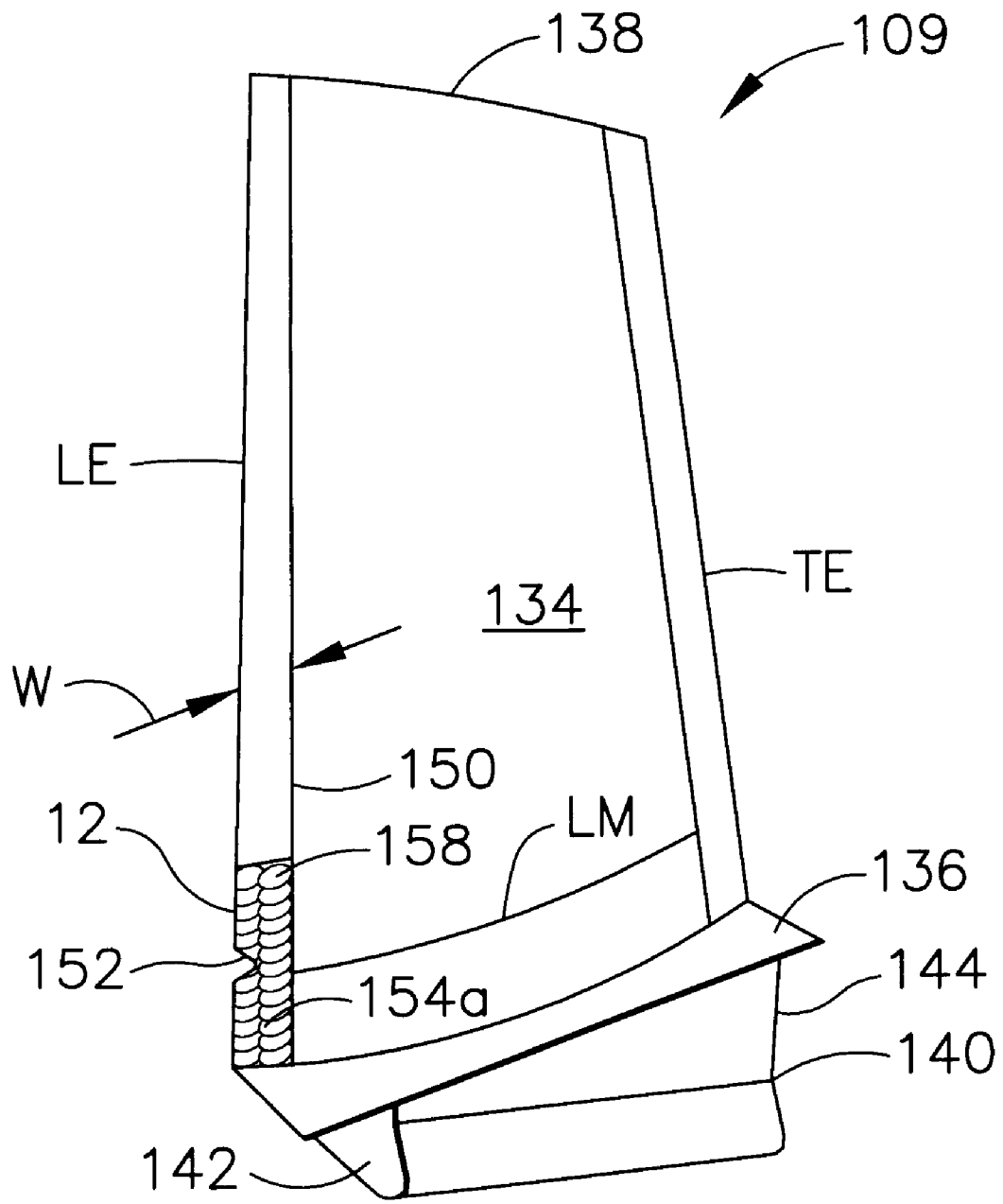
FIG. 9 is a perspective view of a notched fan blade used in the exemplary method of the present invention.

The pre-determined criteria are preferably based on a correlation of optical spectrum test data versus high cycle fatigue data of test versions of the workpieces that are exemplified by laser shock peened and notched test blades 109 illustrated in FIG. 9.

Referring to FIGS. 7 and 8, the production fan blade 108 includes an airfoil 134 extending radially outward from a blade platform 136 to a blade tip 138 and a root section 140 extending radially inward from the platform 136. The root section 140 has a blade root 142 connected to the platform 136 by a blade shank 144. The airfoil 134 extends in the chordwise direction between a leading edge LE and a trailing edge TE of the airfoil. A chord CH of the airfoil 134 is the line between the leading edge LE and trailing edge TE at each cross-section of the blade as illustrated in FIG. 8. A pressure side 146 of the airfoil 134 faces away from the general direction of rotation as indicated by an arrow V and a suction side 148 is on the other side of the airfoil and a mean-line ML is generally disposed midway between the two sides in the chordwise direction.

The production fan blade 108 has a leading edge section 150 that extends along the leading edge LE of the airfoil 134 from the blade platform 136 to the blade tip 138. The leading edge section 150 includes a pre-determined first width W such that the leading edge section 150 encompasses an area where nicks and tears that may occur along the leading edge of the airfoil 134 during engine operation. The airfoil 134 is subject to a significant tensile stress field due to the centrifugal forces generated by the rotation of the fan blade 108 during engine operation. The airfoil 134 is also subject to vibrations generated during engine operation and the nicks and tears operate as high cycle fatigue stress risers producing additional stress concentrations around them.

To counter fatigue failure of portions of the blade along possible crack lines that can develop and emanate from the nicks and tears, the laser shock peened patch 12 is placed along a portion of the leading edge LE where incipient nicks and tears may cause a failure of the blade due to high cycle fatigue. The laser shock peened patch 12 is placed along a portion of the leading edge LE where an exemplary pre-determined first mode line LM of failure may start. Within the laser shock peened patch 12, at least one and preferably both the pressure side 146 and the suction side 148 are simultaneously laser shock peened to form oppositely disposed first and second laser shock peened blade surfaces 154a and 154b and pre-stressed blade regions 156a and 156b, respectively, having deep compressive residual stresses imparted by laser shock peening (LSP) extending into the airfoil 134 from the laser shock peened surfaces as seen in FIG. 8. The pre-stressed blade regions 156a and 156b are illustrated along only a portion of the leading edge section 150, but may extend along the entire leading edge LE or longer portion thereof, if so desired.

The quality assurance method of the present invention is performed during the laser shock peening processing of the production blades 108 and is preferably performed for each laser shot as the laser shock peened patch 12 is formed. Alternatively, the QA test could also be performed on a sacrificial blade or coupon prior to and/or following the laser shock peen processing of a batch of the production blades 108 to provide data for laser shock penn process control. Preferably, the temporal measurements of optical spectrums are made for each plasma 8 formed for each firing of the laser beam 102 with the same laser shock peening processing equipment process parameters beam characteristics, and materials used for the production fan blades 108. This allows an operator on the production line to use this method to examine some or all of the production workpieces for quality assurance in real time and with a minimal impact on the overall production of the workpieces.

Figure 11:
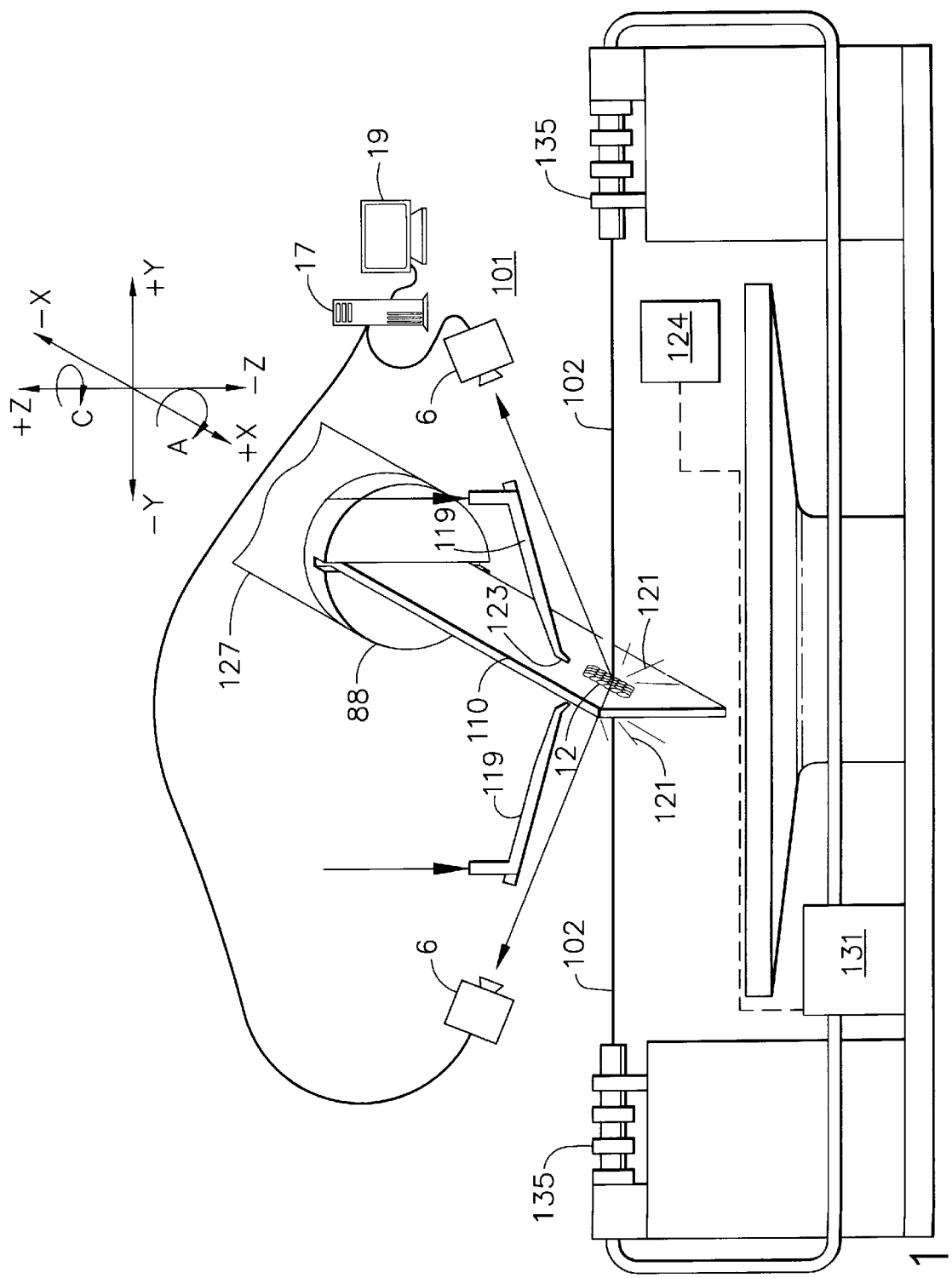
FIG. 11 is a schematic perspective illustration of a test coupon simulating the blade in FIG. 1 mounted in a laser shock peening system in accordance with an alternative embodiment of the present invention.

To provide an evaluation of the effectiveness of the laser shock peening process, a correlation is developed between the spectral/temporal characteristics of each laser shot and the spatial placement of these shots within the laser shock patch, and the fatigue life of the blades processed by this method. A test laser shock peened surface 154 for laser shock peening is used to establish the correlation. The test laser shock peened surface 154 is preferably on the same type of object as the workpiece, in this embodiment it is the test blade 109. Alternatively, a test coupon 110 of the same material and prepared or coated in the same manner as the production workpiece can be used, as illustrated in FIG. 11. These measurements are made, preferably, in the same way during correlation laser shock peening and during production laser shock peening.

The general form of the optical emission spectrum from a laser shock peening plasma is illustrated in FIG. 2 in terms of its light intensity versus optical wave length. Specific spectral details may be captured during the duration of plasma 8 using the streak camera 6. The optical energy is shown as being divided between that emanating in the form of a discrete line structure and that emanating as a more continuous black body radiator like distribution. The relative distribution of energy between these two forms will change with temperature, pressure, and time within the plasma. The relative distribution of energy will also appear to change with changes in the spectral resolution of the detector. The poorer the resolution, the more the line structure will be integrated into the general black body like distribution. The preferred embodiment of the present invention uses fits of instantaneous spectral data from the plasma over time with the black body radiation distributions of energy with temperature, to determine the instantaneous temperature of the plasma. However, a black body like energy distribution based on spectra generated under specific process parameters and using specific sacrificial process materials could be used as well for instantaneous temperature determinations. The relative intensity of the discrete emission lines 24 could also be used in establishing plasma temperature. Note that the purposes of this patent black body radiation distribution is meant to include the various forms of black body radiation distribution discussed herein, including black body like energy distribution, actual measured black body radiation distribution, and idealized black body energy distribution.

Figure 3:
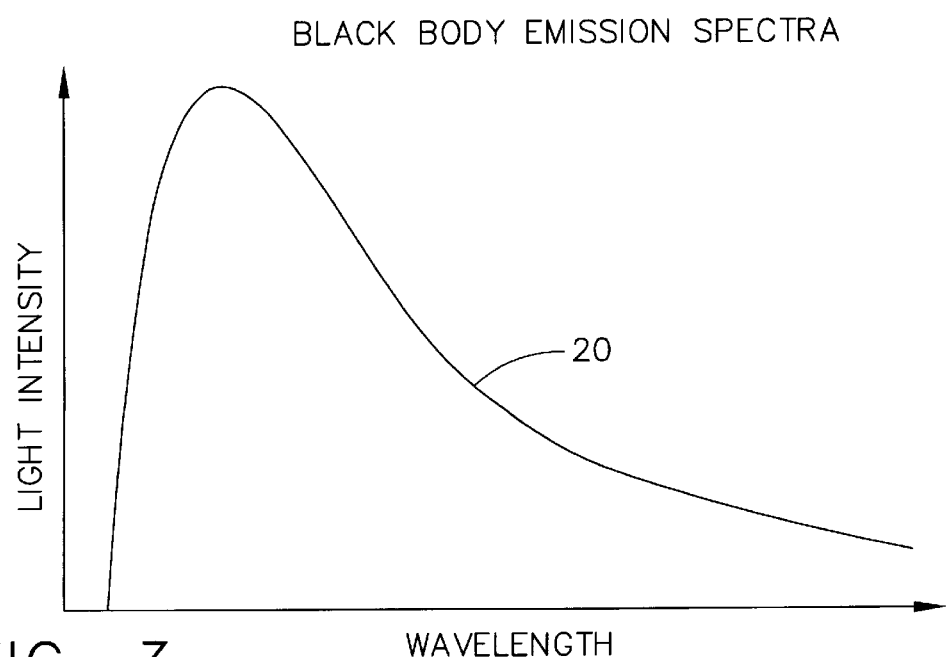
FIG. 3 is an exemplary graphical illustration of the idealized black body radiation from FIG. 2 which is the optical emissions spectra in FIG. 2 with discrete emission lines removed.

Preferably, the discrete emission lines 24 are blocked by selectively masking the spectral image plane to restrict the analyzed spectrum to the black body related components, as shown in FIG. 3, by the black body radiation curve 20. The discrete emission lines 24 may be filtered via a partially transmissive physical filter approximately at the spectral image plane, or computationally filtered via a computerized algorithm with the use of the computer 17 in FIG. 1. The converse is also true in that the desired individual emission lines could be selectively passed by either masking the undesired portion of the spectrum (as described above), or by narrow band pass filtering.

The entire black body like spectrum need not be acquired for determining a fit of the idealized black body energy distribution for peak temperature determination. A few measurements of the intensity of the light within some specifically selected spectral locations (wavelengths) may be sufficient for peak temperature and, therefore, pressure determinations.

Figure 4:
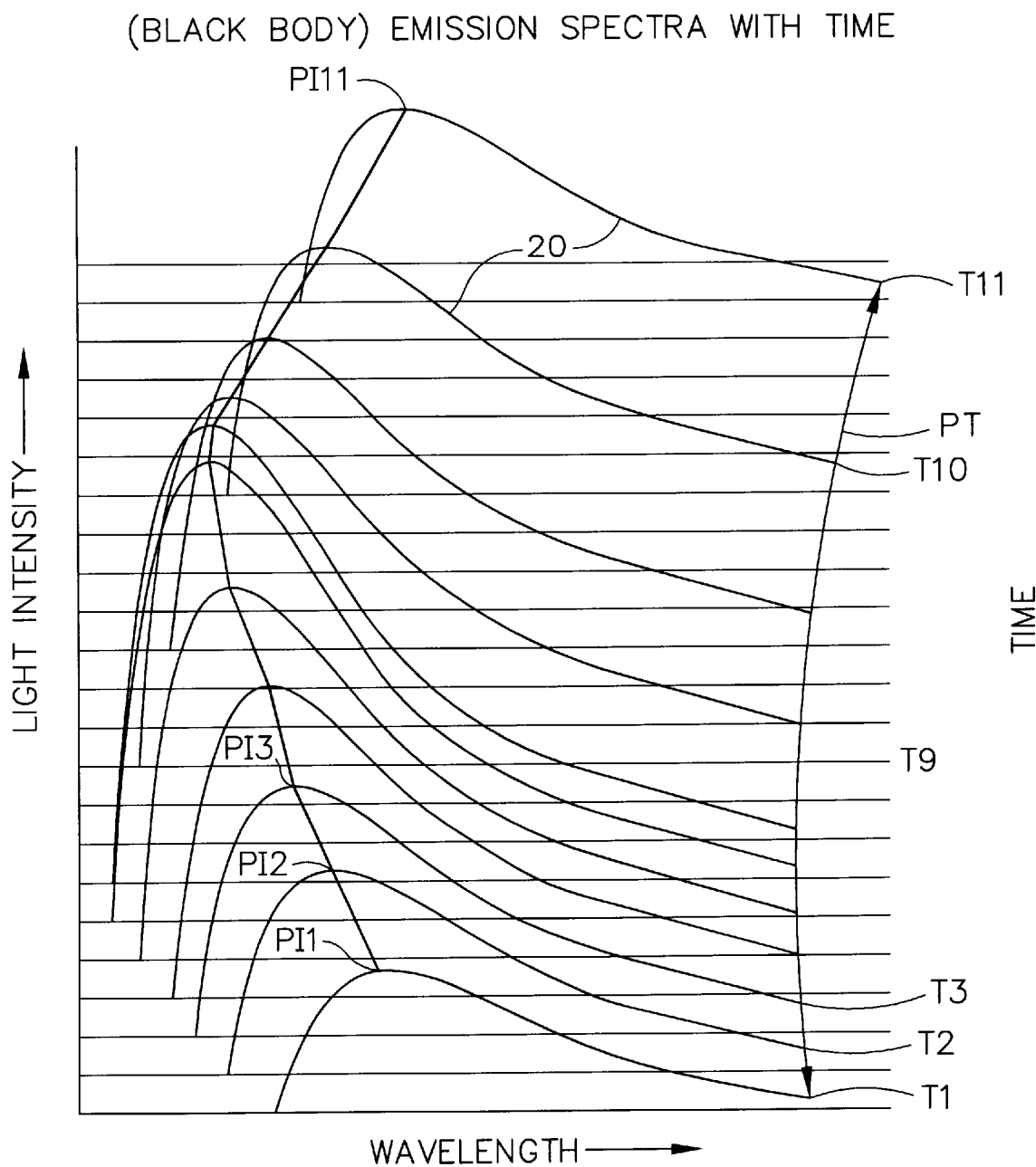
FIG. 4 is an exemplary graphical illustration of black body radiation from several points in time as measured by the system during a period of time in the duration of the plasma in FIG. 1.

FIG. 4 illustrates a series of hypothetical black body like radiation curves 20, representative of the instantaneous optical spectra emitted by the plasma, for a series of first through eleventh points in time T1–T11, respectively, during a period PT of the duration of the plasma 8. Note, that these curves represent processed spectral data or fits of that data to black body like functions, and that for each curve at each of the points in time, there is a corresponding one of first through eleventh peak intensity points PI1–PI11 of the optical emissions spectrums.

Figure 5:
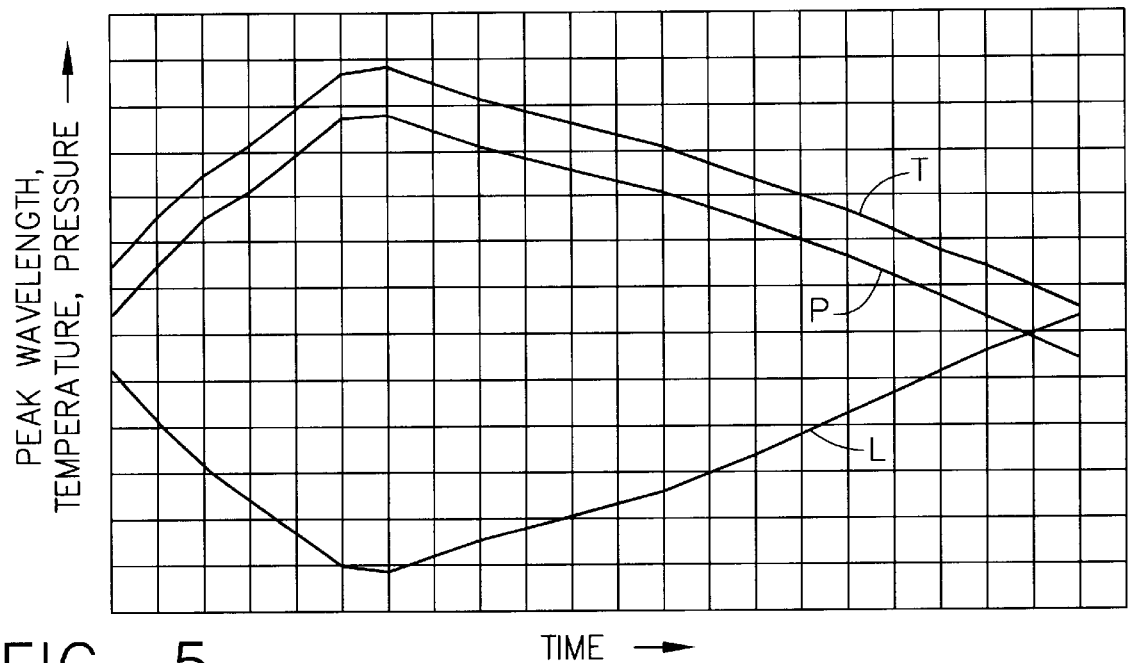
FIG. 5 is an exemplary graphical illustration of the change in black body spectral peak intensity wavelength with two hypothetical plots of plasma temperature and plasma pressure with respect to time during the period during the duration of the plasmin FIG. 1.

FIG. 5 illustrates how the plasma's black body like spectral peak intensity wavelength L and plasma temperature T and plasma pressure P change with time during the period of time PT during the duration of the plasma 8. These parametric temporal spectral functions or curves or distributions are derived from the optical emissions spectra measured by the streak camera 6. One embodiment of the present invention uses one of these parametric curves or distributions as a correlation function for the quality assurance test during production. It is difficult to derive temperature and pressure values from the measured optical emissions spectra measured by the streak camera 6, however, black body or black body like, spectral peak intensity wavelength L, determined from fits of the spectral data to the black body or black body like functions, requires no further complicated calculations. The determination of plasma pressure over time is a desirable relationship to use in establishing the correlation with fatigue life, but the various calculations and empirical studies needed to derive an accurate measurement of the pressure, may not be worth the cost.

The preferred correlation function or curve is a parametric time integrated function or curve for one of the three parametric functions or curves, spectral peak intensity wavelength L, plasma temperature T. or plasma pressure P over the short period of time PT during the duration of the plasma 8 in FIG. 5. The correlation function or correlation curve is derived from any one of the three parametric curves by integrating the parametric function or curve over the period of time PT during the duration of the plasma 8 to derive a time integrated function or curve.

Figure 6:
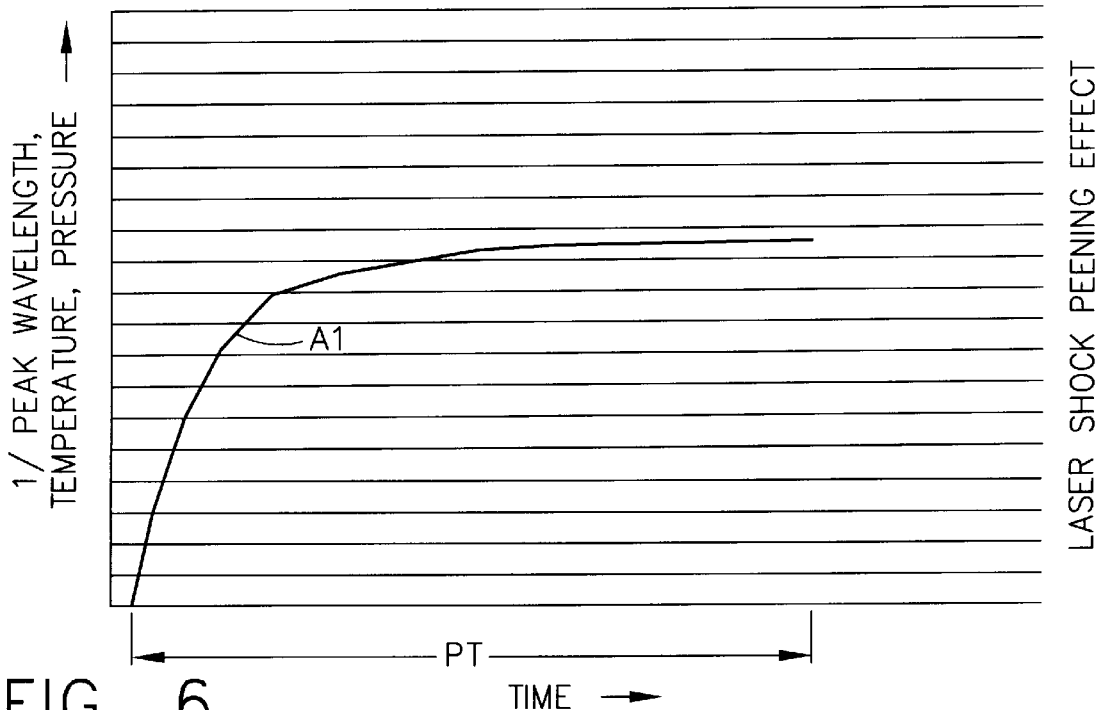
FIG. 6 is an exemplary graphical illustration of the integrated spectral peak intensity wavelength with respect to time during the period during the duration of the plasma in FIG. 1, and its relationship to the magnitude of the laser shock peening effect (scale altered to fit curve).

Illustrated in FIG. 6. is an integrated spectral peak intensity wavelength curve A1 which represents a step in the analysis for one embodiment of the correlation of the present invention. The correlation tests are preferably based on the number of cycles to fatigue failure such as provided by high cycle fatigue (HCF) tests. In the exemplary embodiment herein, the notched test blades 109 are laser shock peened during which temporal measurements of optical spectrums (illustrated in FIG. 2) of the plasma 8 are made at various points, e.g. 5–20 measurements in time during the duration of the plasma, a few nano-seconds, for each firing of the laser beam 102. Then for each firing or laser beam spot an integrated spectral peak intensity wavelength curve A1 such as shown in FIG. 6 is calculated. This yields a plurality B of integrated spectral peak intensity wavelength curves illustrated in FIG. 12 which are then used directly as or to derive a correlation curve or function such as is illustrated in FIG. 13 used during laser shock peening production runs. During laser shock peening production runs of production workpieces, the same spectral measurements and analyze are used to generate production integrated spectral peak intensity wavelength curves that are then compared to the plurality B of integrated spectral peak intensity wavelength curves or a correlation derived from plurality B curves for quality assurance using a go or no go criteria.

The test pieces or test blades 109 are preferably made the same way as the actual production fan blades 108 with a notch 152 added after the test blade 109 is laser shock peened to form the patch 12. After the plurality B of integrated spectral peak intensity wavelength curve plurality is generated or the raw spectral data from the streak camera is recorded and stored, the test blade 109 is vibrated at its first mode frequency until it fails. A number of test blades 109 or just one test blade 109 may be notched and subjected to high cycle fatigue tests to establish the correlation. The notch 152 is representative of a failure precipitating flaw and is placed in the leading edge LE about a pre-determined position of the pre-stressed blade regions 156a and 156b, respectively, after the blade is laser shock peened. Preferably, the notch 152 is also centered about a pre-determined mode line such as the first mode line LM. If it meets standards or test criteria on length of time and amplitude of the forcing function that is exiting the blade, then it is acceptable and its respective plurality B of integrated spectral peak intensity wavelength curves is used for the correlation curve during the quality assurance tests during production runs. It is contemplated that one calibration can be used for an entire production run as long as the production laser shock peening parameters do not change. An alternative embodiment provides for the correlation tests to be based on the number of cycles to fatigue failure produced by low cycle fatigue (LCF).

The spectral analysis during laser shock peening production runs is the same as described above for the correlation runs, but not as many points in time and wavelengths must be analyzed. Several points may be analyzed using the computer 17 and displayed against a correlation on the screen 19 so that production slow down is minimal.

Figure 12:
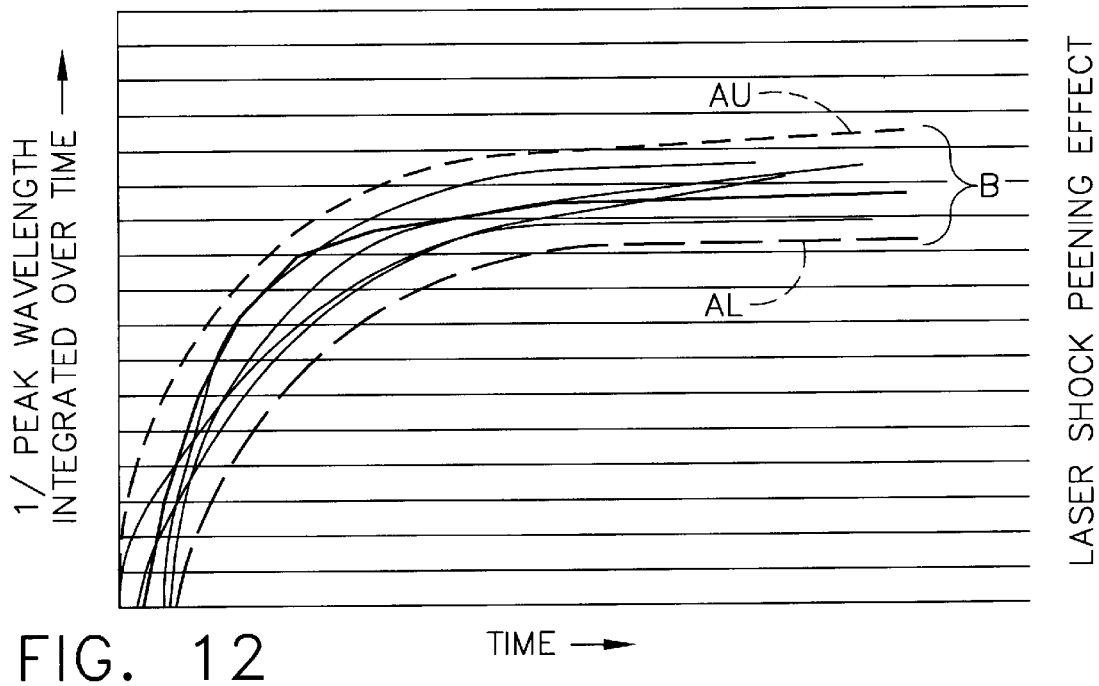
FIG. 12 is an exemplary graphical illustration of a plurality of integrated spectral peak intensity wavelength curves made with test data one of which is illustrated in FIG. 6.
Figure 13:
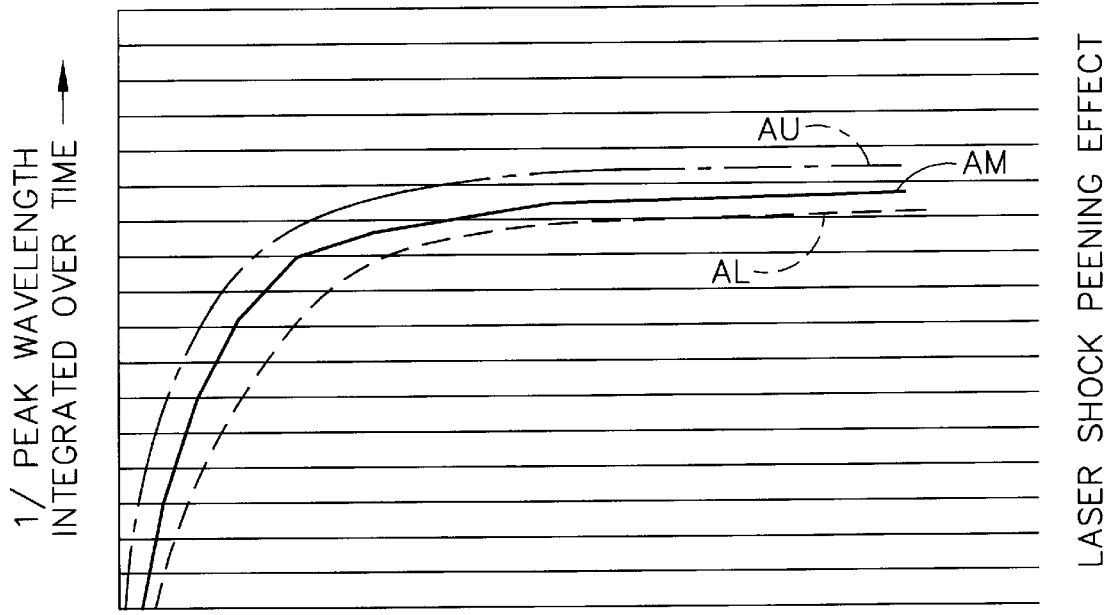
FIG. 13 is an exemplary graphical illustration of a derived correlation curves derived from the plurality of integrated spectral peak intensity wavelength curves illustrated in FIG. 12.

Illustrated in FIG. 12 is one correlation for pass or fail testing of production workpieces having a pass range or band between upper and lower limits. Variations in the laser shock peening process, such as varying laser beam fluence, may be used to establish upper and lower integrated spectral peak intensity wavelength limits AU and AL, respectively, and an integrated spectral peak intensity wavelength mean AM during the testing and development of the correlation from the plurality B of integrated spectral peak intensity wavelength curves illustrated in FIG. 12. This is then used to as the derived correlation curve or function such as is illustrated in FIG. 13 used during laser shock peening production runs. Alternatively, statistical deviations from the ideal correction curve may be analyzed and used to determine pass or fail of production workpieces. Actual data of integrated spectral peak intensity wavelength curves measured and derived from light intensity measurements made by the spectral camera 6 of plasmas during production runs are preferably displayed on the screen 19 for real time QA tests for each blade.

Figure 10:
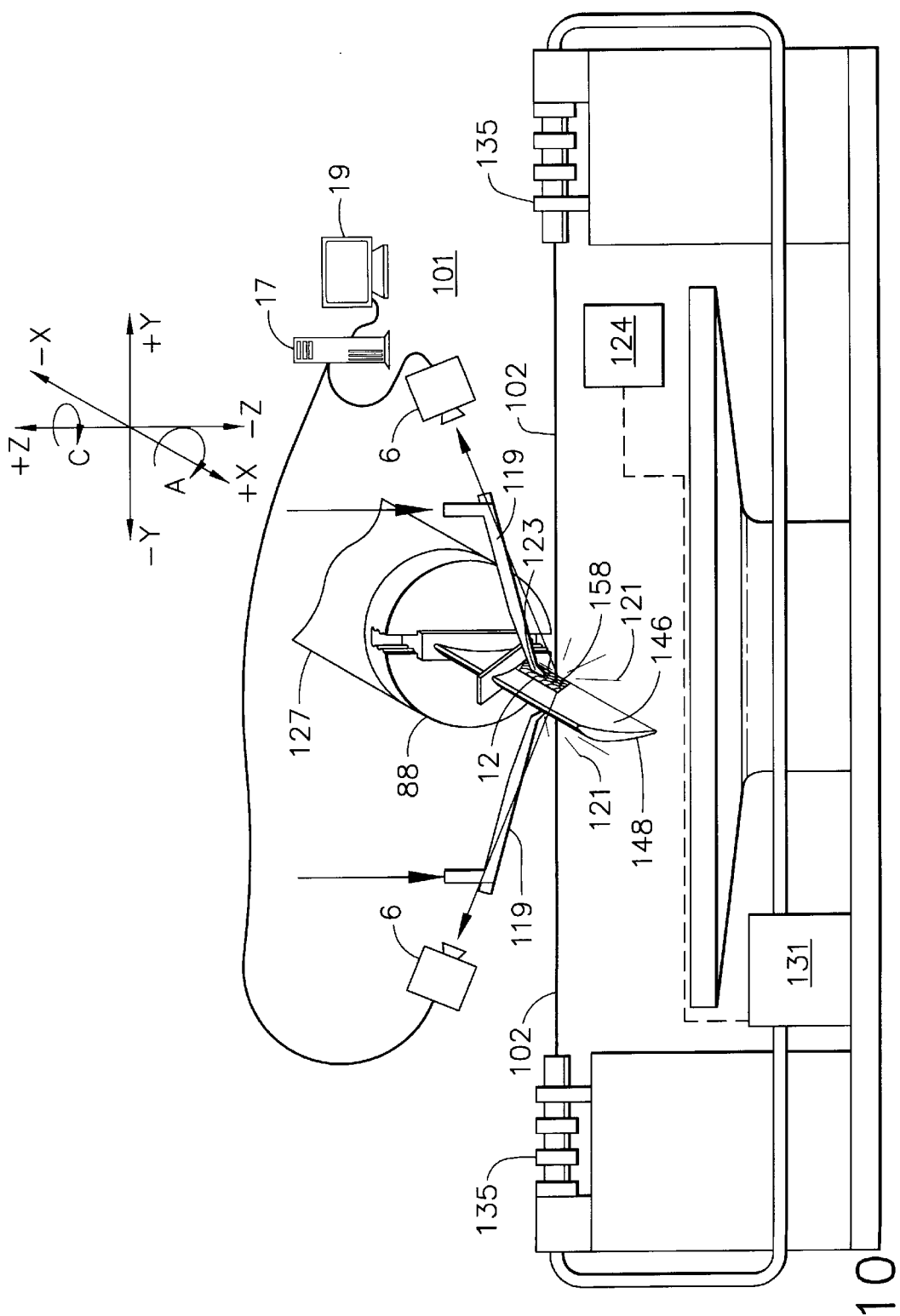
FIG. 10 is a schematic perspective illustration of the blade in FIG. 1 mounted in a laser shock peening system in accordance with an exemplary embodiment of the present invention.

Illustrated in FIGS. 10 and 11 is a laser shock peening system 101 for laser shock peening the production fan blade 108. The production fan blade 108 is mounted in a fixture 88 which is attached to a five-axis computer numerically controlled (CNC) manipulator 127, commercially available from the Huffman Corporation, having an office at 1050 Huffman Way, Clover, S.C. 29710. The five axes of motion that are illustrated in the exemplary embodiment are conventional translational axes X, Y, and Z, and conventional rotational axes A and C that are well known in CNC machining. The manipulator 127 is preferably used to move and position the production fan blade 108 and to effect laser shock peening "on the fly" in accordance with a laser shock peening method and of the present invention. The manipulator 127 is used to continuously move and position the blade to provide laser shock peening "on the fly" in accordance with one embodiment of the present invention. Laser shock peening may be done in a number of various ways using paint or tape as an ablative medium (see—in particular U.S. Pat. No. 5,674,329 entitled "Adhesive Tape Covered Laser Shock Peening"). The same laser shock peening apparatus is used in the laser shock peening process of the patch 12 on the leading edge LE of the production blades 108 and the test blades 109.

The production fan blade 108 may be either continuously or incrementally moved, while incrementally firing the stationary high power laser beams 102 through a curtain of flowing water 121 on the coated surfaces 155, and forming overlapping laser shock peened circular spots 158. The production fan blades 108 are preferably laser shock peened the same way during production runs and HCF testing runs for the correlation. The curtain of water 121 is illustrated as being supplied by a conventional water nozzle 123 at the end of a conventional water supply tube 119. The laser shock peening system 101 has a conventional generator 131 with an oscillator 133 and a pre-amplifier 139A and a beam splitter 143 which feeds the pre-amplified laser beam into two beam optical transmission circuits each having a first and second amplifier 139 and 141, respectively, and optics 135 which include optical elements that transmit and focus the laser beam 102 on the coated surfaces 155. A controller 124 may be used to modulate and control the laser shock peening system 101 to fire the laser beams 102 on the coated surfaces 155 in a controlled manner. Ablated coating material is washed out by the curtain of flowing water 121.

FIG. 11 illustrates an alternative to using actual or representative workpieces during both production runs and calibration runs. The patch 12 is formed on one or more test coupons 110 in at various times during the production run the blades or workpieces being produced. The same type of coupon would be used to generate the correlation curve such as at the beginning of the run after which a laser shock peened and notched blade would be tested for HCF failure to establish the correlation curves and functions illustrated in FIGS. 12 and 13.

It is important to note that the camera 6 can remain fixed just as the position of the laser beam 102 remains fixed while the manipulator 127 orients and moves the production fan blade 108. This feature is very important for the ease of use of the present invention and is, in part, due to the method using relative spectral light intensity data, particularly peak intensity wavelength.

While the preferred embodiment of the present invention has been described fully in order to explain its principles, it is understood that various modifications or alterations may be made to the preferred embodiment without departing from the scope of the invention as set forth in the appended claims.

What is claimed is:

1. A method for quality control testing of a laser shock peening process of production workpieces, said method comprising the following steps:
   (a) firing at least one laser beam pulse from a laser shock peening apparatus on a metallic surface associated with the workpiece and forming a plasma having a duration in which the plasma causes a region to form beneath the surface, the region having deep compressive residual stresses imparted by the laser shock peening process,
   (b) measuring a plurality of optical emissions spectrums radiated by the plasma at a corresponding plurality of times during a period of time during the duration of the plasma, and
   (c) comparing relative distributions of energy within the spectrums to pass or fail criteria for accepting or rejecting the workpieces.

2. A method as claimed in claim 1 wherein the metallic surface is on the production workpiece and correlation is based on high cycle fatigue tests of test pieces that are essentially the same as the production piece and that were laser shock peened in the same or similar laser shock peening apparatus.

3. A method as claimed in claim 1 wherein the pass or fail criteria is a correlation of similar relative distributions of energy within the optical emissions spectrums versus high fatigue failure data.

4. A method as claimed in claim 1 wherein:
the relative distributions of energy within the spectrums is a black body radiation peak intensity wavelength distribution with respect to time during the period of time,
the peak intensity wavelength distribution is obtained by determining a peak intensity wavelength for each of the optical emissions spectrums, and
said comparing relative distributions of energy within the spectrums comprises comparing black body radiation peak intensity wavelength data from the peak intensity wavelength distribution to the pass or fail criteria for accepting or rejecting the workpieces.

5. A method as claimed in claim 4 wherein the pass or fail criteria is a correlation of peak intensity wavelength test data versus high cycle fatigue failure test data for accepting or rejecting the workpieces.

6. A method as claimed in claim 4 wherein the pass or fail criteria is a correlation of peak intensity wavelength test data versus low cycle fatigue failure test data for accepting or rejecting the workpieces.

7. A method as claimed in claim 4 wherein the pass or fail criteria is a correlation of peak intensity wavelength test data integrated over the period of time during the duration of the plasma versus high cycle fatigue failure test data for accepting or rejecting the workpieces.

8. A method as claimed in claim 7 wherein the test pieces each have a failure precipitating flaw within a laser shock peened area of each of the test pieces that was laser shock peened in the same or similar laser shock peening apparatus.

9. A method as claimed in claim 1 wherein the metallic surface is on a metallic coupon made of a material that is the same as or is similar to that of the production workpieces.

10. A method for quality control testing of a laser shock peening process of production workpieces, said method comprising the following steps:
(a) laser shock peening a surface of the production workpiece by firing a plurality of laser beam pulses from a laser shock peening apparatus on a surface of the production workpiece and forming a plurality of plasmas, each one of said plasmas for each of said pulses having a duration in which the plasma causes a region to form beneath the surface, the region having deep compressive residual stresses imparted by the laser shock peening process,
(b) measuring a plurality of optical emissions spectrums radiated by each plasma of at least a portion of said plasmas at a corresponding plurality of times during a period of time during the duration of the plasma, and
(c) comparing relative distributions of energy within the spectrums for each of said plasma to pass or fail criteria for accepting or rejecting the workpieces.

11. A method as claimed in claim 10 wherein the pass or fail criteria is a correlation of similar relative distributions of energy within the optical emissions spectrums versus high fatigue failure data.

12. A method as claimed in claim 10 wherein:
the relative distributions of energy within the spectrums is a black body radiation peak intensity wavelength distribution with respect to time during the period of time,
the peak intensity wavelength distribution is obtained by determining a peak intensity wavelength for each of the optical emissions spectrums, and
said comparing relative distributions of energy within the spectrums comprises comparing black body radiation peak intensity wavelength data from the peak intensity wavelength distributions to the pass or fail criteria for accepting or rejecting the workpieces.

13. A method as claimed in claim 12 wherein the pass or fail criteria is a correlation of peak intensity wavelength test data versus high fatigue failure test data for accepting or rejecting the workpieces.

14. A method as claimed in claim 12 wherein the pass or fail criteria is a correlation of peak intensity wavelength test data integrated over the period of time during the duration of the plasma versus high fatigue failure test data for accepting or rejecting the workpieces.

15. A method as claimed in claim 14 wherein the test pieces each have a failure precipitating flaw within a laser shock peened area of each of the test pieces that was laser shock peened in the same or similar laser shock peening apparatus.

16. A method for quality control testing of a laser shock peening process of gas turbine engine production blades, said method comprising the following steps:
(a) firing at least one laser beam pulse from a laser shock peening apparatus on a metallic surface associated with each of the production blades and forming a plasma having a duration in which the plasma causes a region to form beneath the surface, the region having deep compressive residual stresses imparted by the laser shock peening process,
(b) measuring a plurality of optical emissions spectrums radiated by the plasma at a corresponding plurality of times during a period of time during the duration of the plasma, and
(c) comparing relative distributions of energy within the spectrums to pass or fail criteria for accepting or rejecting the production blades.

17. A method as claimed in claim 16 wherein the metallic surface is on each of the production blades and correlation is based on high cycle fatigue tests of test blades that are essentially the same as the production blades and that were laser shock peened in the same or similar laser shock peening apparatus.

18. A method as claimed in claim 16 wherein the pass or fail criteria is a correlation of similar relative distributions of energy within the optical emissions spectrums versus high fatigue failure data of the test blades.

19. A method as claimed in claim 16 wherein:
the relative distributions of energy within the spectrums is a black body radiation peak intensity wavelength distribution with respect to time during the period of time,
the peak intensity wavelength distribution is obtained by determining a peak intensity wavelength for each of the optical emissions spectrums, and
said comparing relative distributions of energy within the spectrums comprises comparing black body radiation peak intensity wavelength data from the peak intensity wavelength distribution to the pass or fail criteria for accepting or rejecting the production blades.

20. A method as claimed in claim 19 wherein the pass or fail criteria is a correlation of peak intensity wavelength test data versus high cycle fatigue failure test data from the test blades for accepting or rejecting the production blades.

21. A method as claimed in claim 19 wherein the pass or fail criteria is a correlation of peak intensity wavelength test data versus low cycle fatigue failure test data from the test blades for accepting or rejecting the production blades.

22. A method as claimed in claim 19 wherein the pass or fail criteria is a correlation of peak intensity wavelength test data integrated over the period of time during the duration of the plasma versus high cycle fatigue failure test data from the test blades for accepting or rejecting the production blades.

23. A method as claimed in claim 22 wherein the metallic surfaces of the production blades and test blades are along at least a portion of the leading edges of the blades and the test blades each have a failure precipitating flaw within a laser shock peened area of each of the test blades that was laser shock peened in the same or similar laser shock peening apparatus.

24. A method as claimed in claim 23 wherein the failure precipitating flaw is a notch in the portion of the leading edges of the test blades.

* * * * *